US012605276B2

(12) United States Patent  (10) Patent No.:  US 12,605,276 B2

Blazevich  (45) Date of Patent:  Apr. 21, 2026

(54) EYE DROP DISPENSER

(71) Applicant: John Z. Blazevich, Palos Verdes Peninsula, CA (US)

(72) Inventor: John Z. Blazevich, Palos Verdes Peninsula, CA (US)

( * ) Notice: Subject to any disclaimer, the term of this patent is extended or adjusted under 35 U.S.C. 154(b) by 0 days.

(21) Appl. No.: 19/303,843

(22) Filed: Aug. 19, 2025

(65) Prior Publication Data

US 2026/0053665 A1  Feb. 26, 2026

Related U.S. Application Data

(63) Continuation of application No. 18/800,555, filed on Aug. 12, 2024, now Pat. No. 12,414,874, which is a continuation of application No. 18/535,817, filed on Dec. 11, 2023, now Pat. No. 12,070,415.

(51) Int. Cl.
A61F 9/00  (2006.01)
B65D 47/18  (2006.01)

(52) U.S. Cl.
CPC .................................. A61F 9/0026 (2013.01)

(58) Field of Classification Search
CPC .................. A61F 9/0026; A61F 9/0008; A61F 2250/0097; A61F 2230/0063; B65D 47/18; B65D 1/0223; B65D 1/08; B65D 47/2031; A61H 35/02; A61H 2201/0153; A61H 2033/048; A61M 2210/0612; A61M 11/008; A61L 12/086
See application file for complete search history.

(56) References Cited

U.S. PATENT DOCUMENTS

| | | | |
|---|---|---|---|
| 2,209,192 A | 7/1940 | Demsey | |
| 2,231,112 A | 2/1941 | Conner | |
| 2,516,818 A | 7/1950 | West | |
| 2,826,194 A | 3/1958 | Seymour | |
| 3,058,466 A | * 10/1962 | Routsong | .............. A61F 9/0026 |
| | | | D24/128 |
| 3,223,289 A | 12/1965 | Bouet | |

(Continued)

FOREIGN PATENT DOCUMENTS

| | | |
|---|---|---|
| AU | 1388392 A | 2/1993 |
| CA | 132553 S | 5/2010 |

(Continued)

OTHER PUBLICATIONS

Anonymous: "Lansier—Del 23 al 25 de Agosto, 2018 se llevó a cabo el XXVII Congreso Peruano de Oftalmología en el Hotel Westin", Oct. 11, 2018, Retrieved from the Internet: URL: https://www.facebook.com/lansieroeru/posts/683669075353022/.

(Continued)

*Primary Examiner* — Rebecca E Eisenberg
*Assistant Examiner* — Brandon W. Levy
(74) *Attorney, Agent, or Firm* — Knobbe, Martens, Olson & Bear, LLP

(57) ABSTRACT

A dispenser assembly includes a dispenser bottle having a nipple for dispensing a solution (e.g., eye drop solution, eye wash solution, eye lid cleaner and/or wash solution), and a cap removably couplable to the dispenser bottle over the nipple. An eye cup is fixedly coupled to the dispenser bottle around the nipple. The eye cup can be supported on or rest on the periphery of the eye socket to facilitate delivery of the solution onto or over a user's eye.

11 Claims, 11 Drawing Sheets

(56) References Cited

U.S. PATENT DOCUMENTS

| | | | |
|---|---|---|---|
| 3,872,865 | A | 3/1975 | Casey |
| 3,945,381 | A | 3/1976 | Silver |
| 4,002,168 | A | 1/1977 | Petterson |
| 4,085,750 | A | 4/1978 | Bosshold |
| 4,468,103 | A | 8/1984 | Meckler |
| 4,685,906 | A | 8/1987 | Murphy |
| 4,733,802 | A | 3/1988 | Sheldon |
| 4,792,334 | A | 12/1988 | Py |
| 4,805,750 | A | 2/1989 | Nitz |
| 4,909,801 | A | 3/1990 | Casey et al. |
| 4,960,407 | A | 10/1990 | Cope |
| 5,007,905 | A | 4/1991 | Bauer |
| D330,418 | S | 10/1992 | Carter |
| 5,207,657 | A | 5/1993 | Gibilsco |
| 5,221,027 | A | 6/1993 | Gibilsco |
| 5,295,981 | A * | 3/1994 | Smith .................. A61F 9/0026 |
| | | | 604/301 |
| 5,497,910 | A | 3/1996 | Meadows |
| 5,578,021 | A | 11/1996 | Cornish |
| 5,611,788 | A | 3/1997 | Marchment |
| 5,902,292 | A | 5/1999 | Feldman |
| 6,033,384 | A | 3/2000 | Py |
| D424,690 | S | 5/2000 | Szabo |
| D426,300 | S | 6/2000 | Conforti |
| D445,178 | S | 7/2001 | Cogger |
| 6,371,945 | B1 | 4/2002 | Sherman |
| 6,423,040 | B1 | 7/2002 | Benktzon et al. |
| 6,508,793 | B1 | 1/2003 | Harrold |
| D498,415 | S | 11/2004 | Schuller |
| D545,203 | S | 6/2007 | Perry |
| D550,355 | S | 9/2007 | Racz |
| D575,643 | S | 8/2008 | Florio |
| D592,957 | S | 5/2009 | David |
| D596,945 | S | 7/2009 | Barnett |
| D604,166 | S | 11/2009 | Gallo |
| D628,490 | S | 12/2010 | Sato et al. |
| D651,903 | S | 1/2012 | Teller |
| 8,216,195 | B2 | 7/2012 | Wu |
| D681,478 | S | 5/2013 | Riffe |
| D758,867 | S | 6/2016 | Tsai |
| 9,763,826 | B2 | 9/2017 | Cooper |
| D820,001 | S | 6/2018 | Cannamela |
| 9,999,540 | B2 * | 6/2018 | Yang .................... A61F 9/0008 |
| 10,053,245 | B2 | 8/2018 | Leistner et al. |
| D840,821 | S | 2/2019 | Kokubo |
| D887,845 | S | 6/2020 | LaPierre |
| 11,628,089 | B2 | 4/2023 | Gamboa Burgos |
| D985,396 | S | 5/2023 | Matsubara |
| 11,759,797 | B2 | 9/2023 | Greiner-Perth |
| 11,826,281 | B1 | 11/2023 | Blazevich |
| D1,007,680 | S | 12/2023 | Blazevich |
| 12,070,415 | B1 | 8/2024 | Blazevich |
| D1,045,610 | S | 10/2024 | Blazevich |
| 12,127,978 | B1 | 10/2024 | Blazevich |
| D1,060,662 | S | 2/2025 | Blazevich |
| 2004/0007556 | A1 | 1/2004 | Manera |
| 2005/0101921 | A1 | 5/2005 | Sherman |
| 2007/0045354 | A1 | 3/2007 | Boyd et al. |
| 2007/0073231 | A1 | 3/2007 | Lee |
| 2007/0086507 | A1 | 4/2007 | Kim |
| 2007/0233020 | A1 | 10/2007 | Hearne |
| 2008/0208148 | A1 | 8/2008 | Soon |
| 2010/0145287 | A1 | 6/2010 | Grevin |
| 2012/0310184 | A1 | 12/2012 | Pedersen |
| 2013/0096517 | A1 | 4/2013 | Leistner |
| 2013/0220967 | A1 | 8/2013 | Wang |
| 2014/0350492 | A1 | 11/2014 | Rojas |
| 2015/0351960 | A1 | 12/2015 | Cooper |
| 2016/0038339 | A1 | 2/2016 | Behan |
| 2016/0089526 | A1 | 3/2016 | Hofland |
| 2017/0129659 | A1 | 5/2017 | Spiegelhoff |
| 2019/0127119 | A1 | 5/2019 | Kokubo |
| 2021/0378863 | A1 | 12/2021 | Gamboa Burgos |
| 2022/0151829 | A1 | 5/2022 | Henderson |
| 2024/0091058 | A1 | 3/2024 | Nagel |
| 2024/0409281 | A1 | 12/2024 | Heinzle |

FOREIGN PATENT DOCUMENTS

| | | |
|---|---|---|
| CN | 1129301157 A | 6/2021 |
| ES | 2060969 T3 | 12/1994 |
| ES | 1078238 U | 12/2012 |
| ES | 2529056 T3 | 2/2015 |
| JP | 2012065874 A | 4/2012 |
| JP | 2019217056 A | 12/2019 |
| WO | WO 2020/025515 A1 | 2/2020 |
| WO | WO 2020/080962 A1 | 4/2020 |
| WO | WO 2020/214135 A1 | 10/2020 |

OTHER PUBLICATIONS

Autodrop Eye Drop Guide, Caregiversproducts.com, [Post date: Dec. 5, 2012], [Site seen May 11, 2023], Seen at URL: https://www.caregiverproducts.com/autodrop-eye-drop-guide.html (Year: 2012).

Eye Guide Aid, Eyedrop Bottle Dispenser, first available Dec. 13 2022, amazon.ca, [online], [site visited Sep. 24, 2024], Available from internet URL: https://www.amazon.ca/dp/BOBPXRM3CH/ (Year: 2022).

International Search Report and Written Opinion for dated Mar. 24, 2025, issued in corresponding PCT Patent Application No. PCT/US2024/057440.

International Search Report and Written Opinion dated Mar. 28, 2025, issued in corresponding PCT Patent Application No. PCT/US2024/057483.

International Search Report for International Application No. PCT/PE2018/000022 dated May 22, 2019.

Moorfields Eye Hospital NHS Foundation Trust, Opticare, Feb. 19, 2019, Youtube Video retrieved Feb. 25, 2025 (Year: 2019).

Opticare Eye Dropper Dispenser, McArthur Medical Sales, [Post date: unknown], [Site seen at URL: https://mmsiestore.com/product/opticare-eye-dropper-dispenser/ (Year: 2023).

Rhoto All-in-One Lubricant redness reliever, Thoto, rohotoeyedrops.com, {Post date: Sep. 30, 2022}, {Site|seen May 11, 2023], Seen at URL: https://rohtoeyedrops.com/products-rohto-all-in-one-multi-symptopm-eye-drops (Year: 2022).

These Japanese Eye Drops Give My Face Instant Energy, first available Mar. 28, 2017, nymag.com, [online], [site visited Sep. 23, 2024], Available from internet URL: https://nymag.com/strategisUarticle/best-eye-drops-for-reducing-redness-rohto-eye-drops-review.html (Year: 2017).

\* cited by examiner

EYE DROP DISPENSER

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application is a continuation of U.S. patent application Ser. No. 18/800,555, filed on Aug. 12, 2024, which is a continuation of U.S. patent application Ser. No. 18/535,817, filed on Dec. 11, 2023, now U.S. Pat. No. 12,070,415, issued Aug. 27, 2024, the entire disclosure of both of which is incorporated herein by reference.

FIELD

The present disclosure is directed to an eye drop or eye wash or eye lid cleaner dispenser bottle, and more particularly to an eye drop or eye wash or eye lid cleaner dispenser with an eye cup for dispensing eye drops or eye wash or eye lid cleaner.

DESCRIPTION OF THE RELATED ART

Eye drops are regularly used to treat eye conditions such as dry eye, bacterial infections, eye injury, or eye conditions such as glaucoma and cataracts. Existing eye drop dispensers are deficient in that they do not accurately or consistently deliver the drops into the eye (e.g., affecting children and elderly people more), often delivering the drops on other parts of the user's face, leading to multiple attempts and making the solution difficult to administer. These multiple attempts cause an unnecessary wasting of the eye drops, thereby costing the consumer more. Another deficiency of existing eye drop dispensers is that user's may contaminate existing eye drop dispensers by touching their eye or face with the dispenser causing bacteria to grow on the dispenser tip and leading to eye infections. When the user suffers from hand tremors (e.g., essential tremor disorder or other neurological conditions) which cause shaking hands while trying to deliver the eye drops, the tremors exacerbate the defects of existing eye drop dispensers. Because existing dispenser designs make delivering eyedrops difficult, there is a decrease in compliance by users to take their medication.

SUMMARY

The systems, methods, and devices described herein have innovative aspects, no single one of which is indispensable or solely responsible for their desirable attributes. Without limiting the scope of the claims, some of the advantageous features will now be summarized.

In some aspects, the techniques described herein relate to an eye drop dispenser assembly, including: a dispenser bottle having a nipple via which a solution is dispensed, the nipple projecting from a surface of the dispenser bottle, and a cap removably couplable to the dispenser bottle over the nipple. The cap having an outer cap, an inner cap extending within the outer cap, and a seal recessed in a hollow end of the inner cap. The assembly also includes an eye cup fixedly coupled to a second surface of the dispenser bottle and configured to fit within the cap when the cap is coupled to the dispenser bottle. The eye cup having a circumferential wall disposed around the nipple and a distal edge of the circumferential wall defining an oval shape. The distal edge configured to be disposed over an eye socket to facilitate delivery of the solution into a user's eye. The nipple disposed between the distal edge of the circumferential wall and the dispenser body. Wherein, when the cap is coupled to the dispenser body, the seal sits adjacent the nipple to inhibit leakage of the solution from the nipple and the distal portion of the inner cap encircles the nipple.

In some aspects, the second surface of the dispenser is coplanar with the surface of the dispenser.

In some configurations, a height of the nipple above the surface of the dispenser is less than half of a height of the eye cup above the second surface.

In some configurations, the nipple is recessed proximal to the dispenser bottle.

In some configurations, the seal comprises rubber.

In some configurations, the dispenser bottle comprises plastic.

In some aspects, the techniques described herein relate to an eye drop dispenser assembly, including: a dispenser body having a nipple through which a solution is dispensed, the nipple projecting from the dispenser body and a cap removably couplable to the dispenser body over the nipple. The cap having a cavity, a post extending within the cavity, and a seal recessed in a hollow end of the post. The assembly also including an eye cup fixedly coupled to the dispenser body and disposed around the nipple. The eye cup having a circumferential wall and a distal edge configured to be disposed over an eye socket to facilitate delivery of a solution into a user's eye. The nipple disposed between the distal edge of the circumferential wall and the dispenser body. Wherein, when the cap is coupled to the dispenser body, the seal inhibits leakage of the solution from the nipple and a distal portion of the post encircles the nipple.

In some configurations, the eye cup is configured to inhibit the nipple from touching the user's eye.

In some configurations, the body has a recess from which the nipple projects opposite the distal edge of the eye cup.

In some configurations, a height of the nipple above the dispenser body is less than half a height of the distal edge of the eye cup above the dispenser body.

In some configurations, the dispenser body has a recess extending away from the distal edge of the eye cup, the nipple projecting towards the distal edge of the eye cup from the recess.

In some configurations, the circumferential wall of the eye cup is partially disposed within the recess.

In some configurations, a distal portion of the post extends past the seal.

In some configurations, a distal portion of the post is couplable to the nipple.

In some configurations, the dispenser body has a shoulder, and the cap is couplable to the dispenser body around the shoulder.

In some configurations, the cap is couplable to the dispenser body with an annular snap fit.

In some aspects, the techniques described herein relate to an eye drop dispenser assembly, including: a dispenser bottle having a nipple via which a solution is dispensed, the nipple projecting from a surface of the dispenser bottle and a cap removably couplable to the dispenser bottle over the nipple. The cap having an outer cap, an inner cap extending within the outer cap, and a seal recessed in the inner cap. The assembly also including an eye cup fixedly coupled to a second surface of the dispenser bottle. The eye cup having a distal edge defining an oval shape, disposed circumferential to the nipple. Wherein, when the cap is coupled to the dispenser body, the seal sits adjacent the nipple.

In some configurations, the eye cup is coupled to the surface.

In some configurations, the dispenser assembly is configured to prevent contamination of the nipple and inadvertent contact of the nipple with the user's eye.

In some configurations, the distal edge of the eye cup is contoured to fit around a periorbital region.

In some configurations, the surface of the bottle is in a recess below a shoulder of the bottle.

In some configurations, the nipple is disposed within the recess.

In some configurations, the distal edge is contoured relative to an axis defined by a periorbital region.

DETAILED DESCRIPTION

Figure 1B:
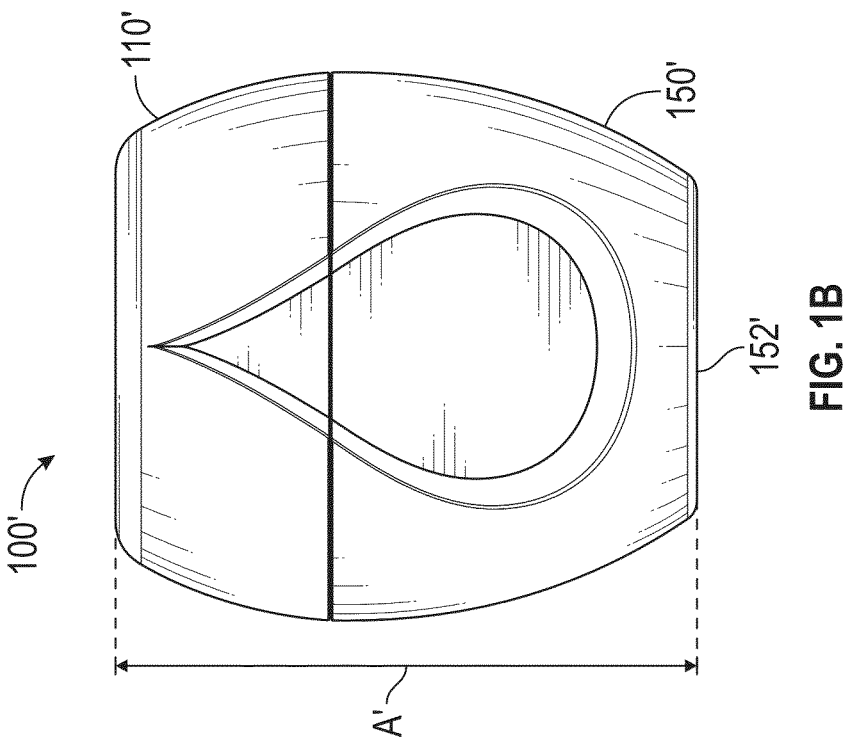
FIG. 1B is a schematic front view of a second embodiment of an eye drop dispenser assembly.

Embodiments of the eye drop dispenser assembly will now be described with reference to the accompanying figures, wherein like numerals refer to like or similar elements throughout. Although several embodiments, examples, and illustrations are disclosed below, it will be understood by those of ordinary skill in the art that the inventions described herein extends beyond the specifically disclosed embodiments, examples, and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

FIGS. 1A, 2A-2C, 4A, and 5C show a dispenser assembly 100 (the "assembly 100"). The assembly 100 includes a dispenser bottle 150 (e.g., dispenser body), an eye cup 140, a nipple 130, and a cap 110. The dispenser bottle 150, the eye cup 140, and/or the cap 110 can optionally be made in part or whole of plastic (e.g., polypropylene), silicone or rubber. However, the dispenser bottle 150, the eye cup 140, and/or the cap 110 can be made of other suitable materials (e.g., flexible or resilient materials). The eye cup 140 may be formed from a clear or transparent material. The dispenser assembly 100 can house and deliver a solution (e.g., eye drops, eye wash, eye lid cleaner and/or wash) onto or over the eye or a portion thereof (e.g., eye lid).

FIGS. 1B, 3A-3C, 4B, and 5D show views of a dispenser assembly 100' (hereafter "the assembly 100'"), which is a compact (e.g., small or pocket sized) version of the dispenser assembly 100. Some of the features of the assembly 100' are similar to features of the assembly 100 in FIGS. 1A, 2A-2C, 4A, and 5C. Thus, reference numerals used to designate the various components of the assembly 100' are identical to those used for identifying the corresponding components of the assembly 100 in FIGS. 1A, 2A-2C, 4A, and 5C, except that a "'" has been added to the numerical identifier. Therefore, the structure and description for the various features of the assembly 100 and how it is operated and controlled in FIGS. 1A, 2A-2C, 4A, and 5C are understood to also apply to the corresponding features of the assembly 100', except as described below. The dispenser assembly 100' can house and deliver a solution (e.g., eye drops, eye wash, eye lid cleaner and/or wash) onto or over the eye or a portion thereof (e.g., eye lid).

The dispenser assembly 100 includes a dispenser bottle 150 with a base 152 and a cap 110 removably couplable to an end of the dispenser bottle 150 opposite to (e.g., distal from) the base 152. In some embodiments, the base 152 is flat. In other embodiments, a portion, but less than all, of the base 152 is flat. The base 152 allows the dispenser bottle 150 to stand upright when not in use which advantageously reduces the amount of fluid (e.g., eye drops, eye wash, eye lid cleaner and/or wash) wasted. The cap 110 is removably coupled to the dispenser bottle 150. The assembly 100 has a height A measured from the base 152 to a top of the cap 110. In one implementation, the height A is between about 2 and 3 inches, such as 2.5 inches.

The dispenser assembly 100' includes a dispenser bottle 150' (e.g., dispenser body) with a base 152' and a cap 110' removably couplable to an end of the dispenser bottle 150' opposite to (e.g., distal from) the base 152'. In some embodiments, the base 152' is flat. In other embodiments, a portion, but less than all, of the base 152' is flat. The assembly 100' has a height A' measured from the base 152' to a top of the cap 110'. In one implementation, the height A' is between about 1.5 and 2.5 inches, such as 2 inches.

Figure 1A:
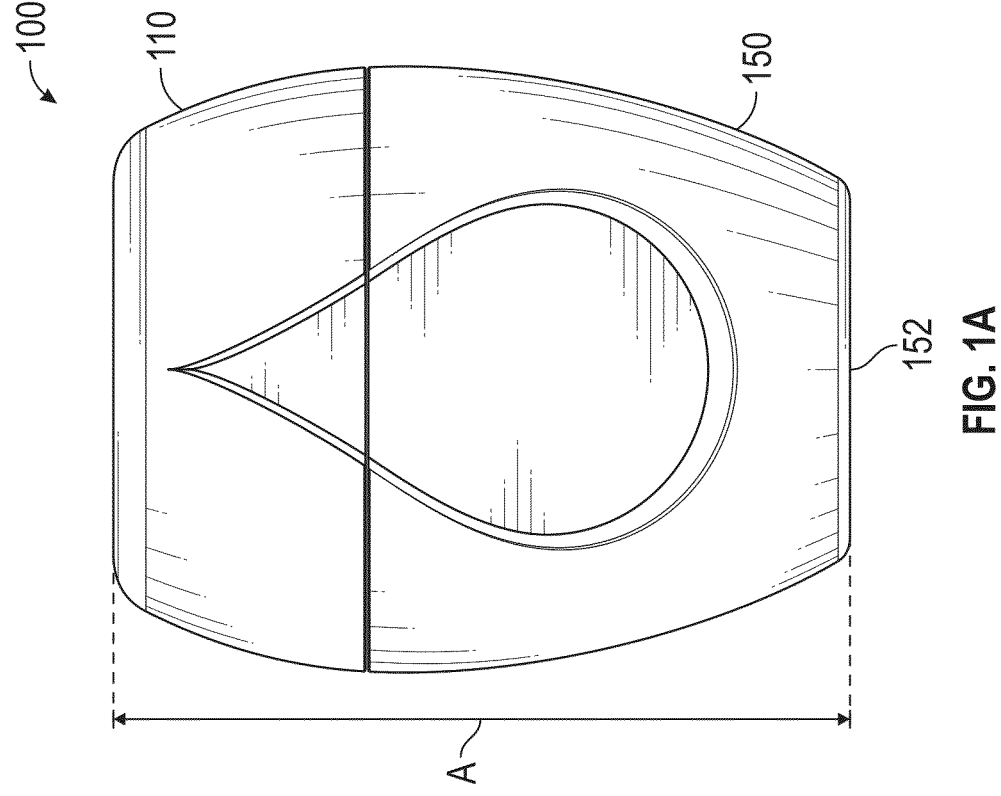
FIG. 1A is a schematic front view of one embodiment of an eye drop dispenser assembly.
Figure 2A:
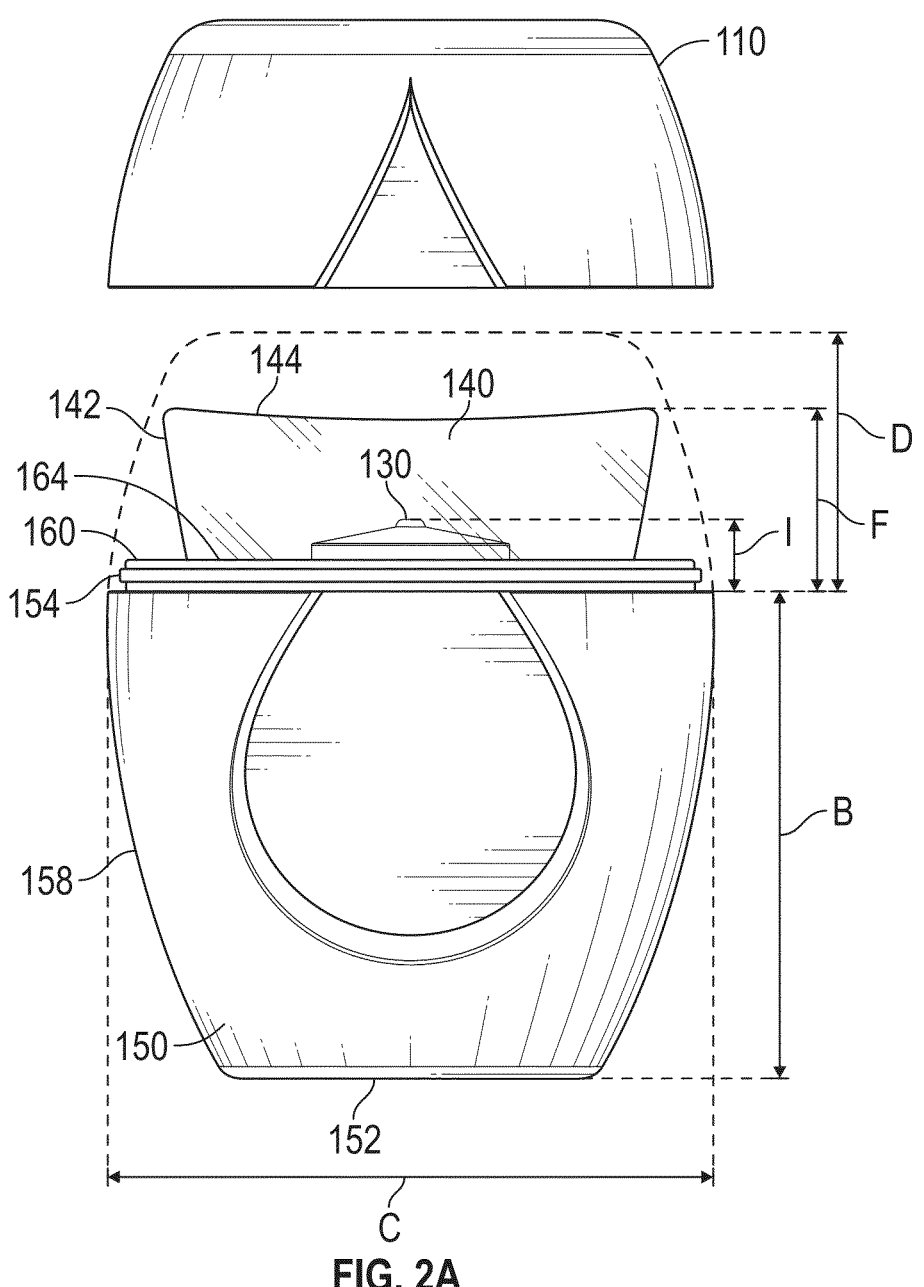
FIG. 2A is a schematic front view of the eye drop dispenser assembly of FIG. 1A with its cap removed and spaced above the dispenser bottle, the dashed line showing the outline of the cap when covering the eye cup.

FIG. 2A depicts a front view of the dispenser assembly 100 shown in FIG. 1A with the cap 110 removed. The dispenser bottle 150 has the base 152 connected to a side wall 158. The side wall 158 is circumferential and extends from the base 152. The dispenser bottle 150 has a nipple 130 projecting from a surface 164 of the dispenser bottle 150 that is at an opposite end of the dispenser bottle 150 (e.g., distal) from the base 152. The nipple 130 can have a circular profile, as shown for example in FIG. 4A; however, the nipple 130 can have other suitable shapes. In some embodiments, the circumferential side wall 158 can flex (e.g., when the dispenser bottle 150 is squeezed). The dispenser bottle 150 also has a shoulder 154 that circumscribes a second surface 160. The second surface 160 connect to the circumferential side wall 158. In the illustrated embodiment the surface 164 is coplanar with the second surface 160. The cap 110 is removably couplable to the dispenser bottle 150 around the shoulder 154. In some examples the cap 110 is removably couplable to the shoulder 154 with an annular snap fit. In some embodiments, the shoulder 154 is disposed to extend above the second surface 160. In other embodiments, the shoulder 154 is formed integral to the second surface 160 (e.g., the second surface 160 forms the upper surface of the shoulder 154 such that when the cap 110 is on, or connects to, the second surface 160 fits within the cap 110 rather than the cap 110 sitting on the second surface 160). In the illustrated arrangement, the assembly 100 also includes an eye cup 140, which provides a supporting structure to the dispenser bottle 150 when it is inverted for delivery of solution on or over the eye (e.g., the eye cup 140 resting on the user's eye socket to support the dispenser bottle 150 in the inverted position). The eye cup 140 is coupled to the second surface 160 of the dispenser bottle 150 (e.g., to an end of the dispenser bottle 150 opposite the base 152). The eye cup 140 can fit within the cap 110 when the cap 110 is coupled to the dispenser bottle 150. In some embodiments, the eye cup 140 is fixedly coupled to the second surface 160 (e.g., so that the eye cup 140 is integral to, and cannot be detached or removed from, the dispenser bottle 150). The eye cup 140 has a circumferential wall 142 that extends to an edge 144 that is distal to the dispenser bottle 150. In one example, the eye cup 140 (e.g., the circumferential wall 142) tapers toward the second surface 160. The circumferential wall 142 defines an oval shape surrounding the nipple 130 (e.g., when the dispenser assembly 100 is viewed from the top with the cap 110 removed, see FIG. 4A. The circumferential wall 142 surrounds the nipple 130, and the nipple 130 is disposed between the distal edge 144 of the circumferential wall and the second surface 160 of the dispenser bottle 150.

The dispenser bottle 150 can optionally be made of plastic, silicone, rubber, or other suitable resilient or flexible material. The dispenser bottle 150 can optionally be a single piece (e.g., a monolithic, seamless single piece). In some embodiments, the base 152, side wall 158, surface 164, second surface 160, shoulder 154, nipple 130, and eye cup 140, or any combination thereof, may be formed as a single piece. The single piece can be an integrated assembly of several parts or can be a unitary structure formed from a single piece of material. In some embodiments, the base 152, side wall 158, surface 164, second surface 160, shoulder 154, nipple 130, and eye cup 140 may be made from plastic, rubber, silicone or any suitable material. Any of these portions may be made from the same material or from different materials.

In the illustrated arrangement, the assembly 100 has a width C. In one implementation, the width C is between 1.5 and 2.5 inches, such as 2 inches. The dispenser bottle 150 has a height B measured from the base 152 to the surface 164. In one implementation, the height B is between 1.25 and 2 inches, such as 1.625 inches. The dispenser bottle 150 also has a height I measured from the surface 164 to the top of the nipple 130. The assembly 100 has a height F measured from the second surface 160 to the distal edge 144. Height F is advantageously larger than height I to inhibit (e.g., prevent) the nipple 130 from contacting the eye 200 when in use. This positioning advantageously prevents (e.g., inhibits) contamination of the nipple 130 or injury to the eye 200 during use. Additionally, in some examples the height I may be less than half of height F which advantageously further reduces the chance that the nipple 130 will inadvertently touch the user's eye 200 or otherwise be contaminated. In one implementation, the height I is between 0 and 0.4 inches, such as 0.2 inches and the height F is between 0.25 and 0.75 inches, such as 0.5 inches. The assembly 100 also has a height D. Height D is the height of the cap 110. In one implementation, height D is greater than height F. In one implementation, the height D is between 0.5 and 1.0 inches, such as 0.875 inches.

Figure 2B:
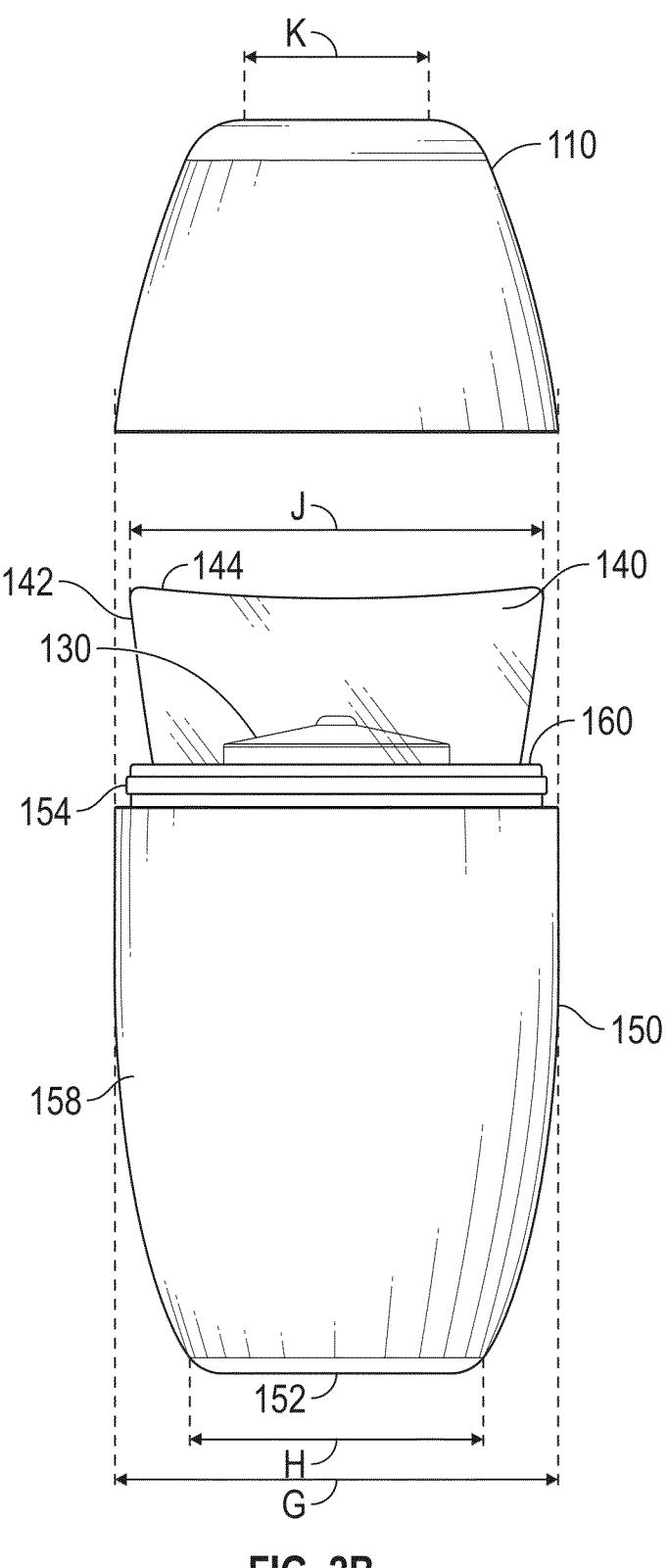
FIG. 2B is a schematic side view of the eye drop dispenser assembly of FIG. 1A with its cap removed and spaced above the dispenser bottle.

With reference to FIG. 2B, the assembly 100 has a depth G. The base 152 has a depth H. Depth G may be larger than depth H. In one implementation, the depth G is between 1 and 1.5 inches, such as 1.25 inches and the depth H is between 0.5 and 1 inch, such as 0.75 inches. The eye cup 140 has a depth J. Depth J may be smaller than Depth G. In one implementation, the depth J is between 1 and 1.25 inches, such as 1.1 inches. The cap 110 has a depth K (at its distal end). In one implementation, the depth K is between 0.5 and 0.75 inches, such as 0.7 inches.

Figure 2C:
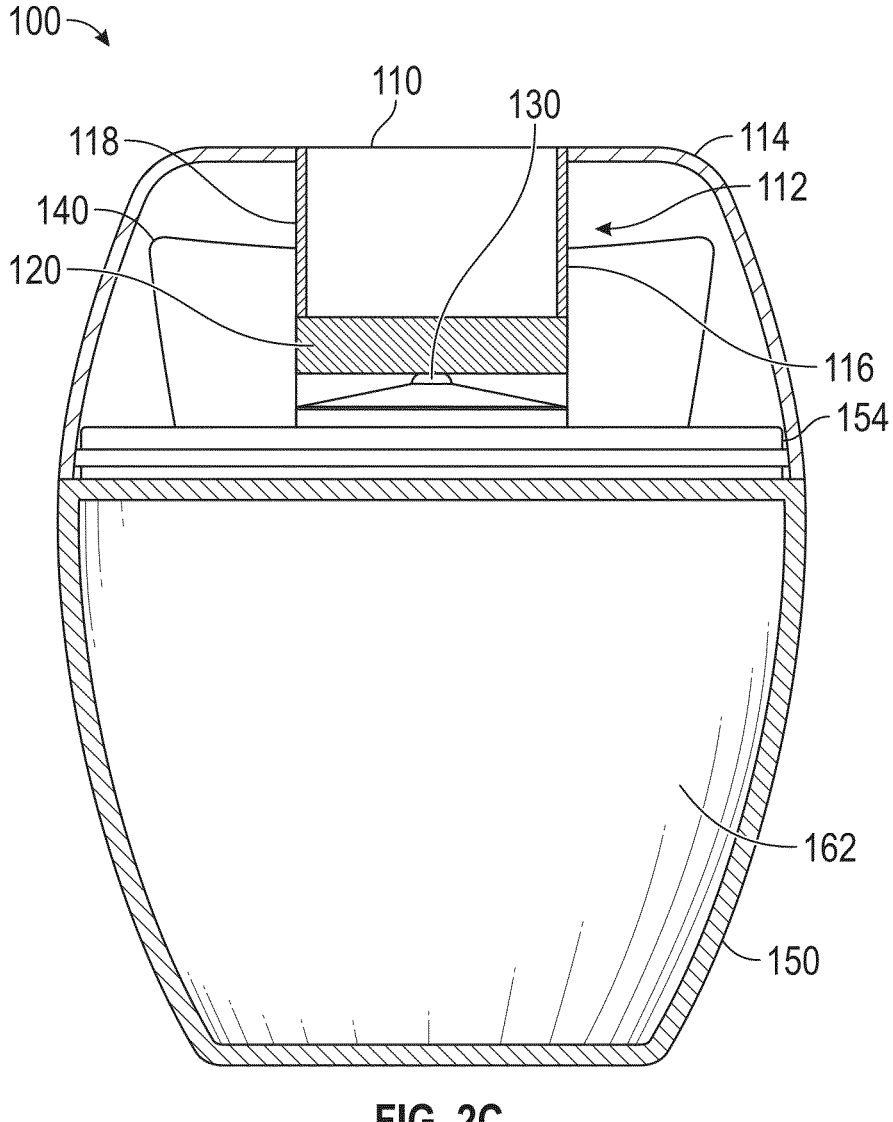
FIG. 2C is a schematic cross-sectional view of the eye drop dispenser assembly of FIG. 1A, where the section line is through the midplane of the side view in FIG. 2B.

FIG. 2C depicts a cross-sectional view of the dispenser assembly 100 shown in FIG. 2A. The section is taken at a midpoint of the depth G of the assembly 100 (see FIG. 2B). The dispenser bottle 150 has a chamber 162 that can hold a liquid solution (e.g., eye drop solution, eye wash solution, eye lid cleaner or wash solution). The cap 110 is connected to the dispenser bottle 150. The eye cup 140 fits within a cavity 112 of the cap 110 when the cap 110 is removably coupled to the dispenser bottle 150. The cap 110 has an outer cap 114 that defines the cavity 112. Within the cavity 112, is a post 118 extending from an underside of the outer cap 114. In one example, the post 118 is solid. In another example, the post 118 includes a hollow portion (e.g., at a distal end of the post 118). The post 118 has a seal 120 at its distal end. In one example, the seal 120 is separate from the post 118 and is disposed within the hollow portion of the post 118. In another example, the seal 120 is separate from the post 118 and is attached to an end of the post 118. In another example, the seal 120 is integral (e.g., one piece, monolithic) with the post 118 (e.g., the seal 120 is a distal portion of the post 118 and made of the same material as the post 118). When the cap 110 is coupled to the dispenser bottle 150, the outer cap 114 is coupled to (e.g., disposed around) the shoulder 154 of the dispenser bottle 150. The post 118 and the seal 120 define an inner cap 116 that is coupled to (e.g., disposed around) the nipple 130 so that a distal portion of the post 118 encircles the nipple 130 and is coupled to the nipple 130. The seal 120 sits adjacent the top of the nipple 130 and presses against the nipple 130 to inhibit (e.g., prevent) leakage of solution from the nipple 130. In another example, when the cap 110 is coupled to the dispenser bottle 150, the seal 120 at the end of the post 118 engages (e.g., contacts) the nipple 130 to inhibit (e.g., prevent) leakage of solution from the dispenser bottle 150. In one example, the seal 120 can have a shape similar to (e.g., a mirror image of) a shape of the nipple 130). The post 118 is disposed within the eye cup 140 when the cap 110 is connected to the dispenser bottle 150 (e.g., when the cap 110 is coupled to the dispenser bottle 150 the post 118 is surrounded by the eye cup 140, which is surrounded by the outer cap 114).

Figure 3A:
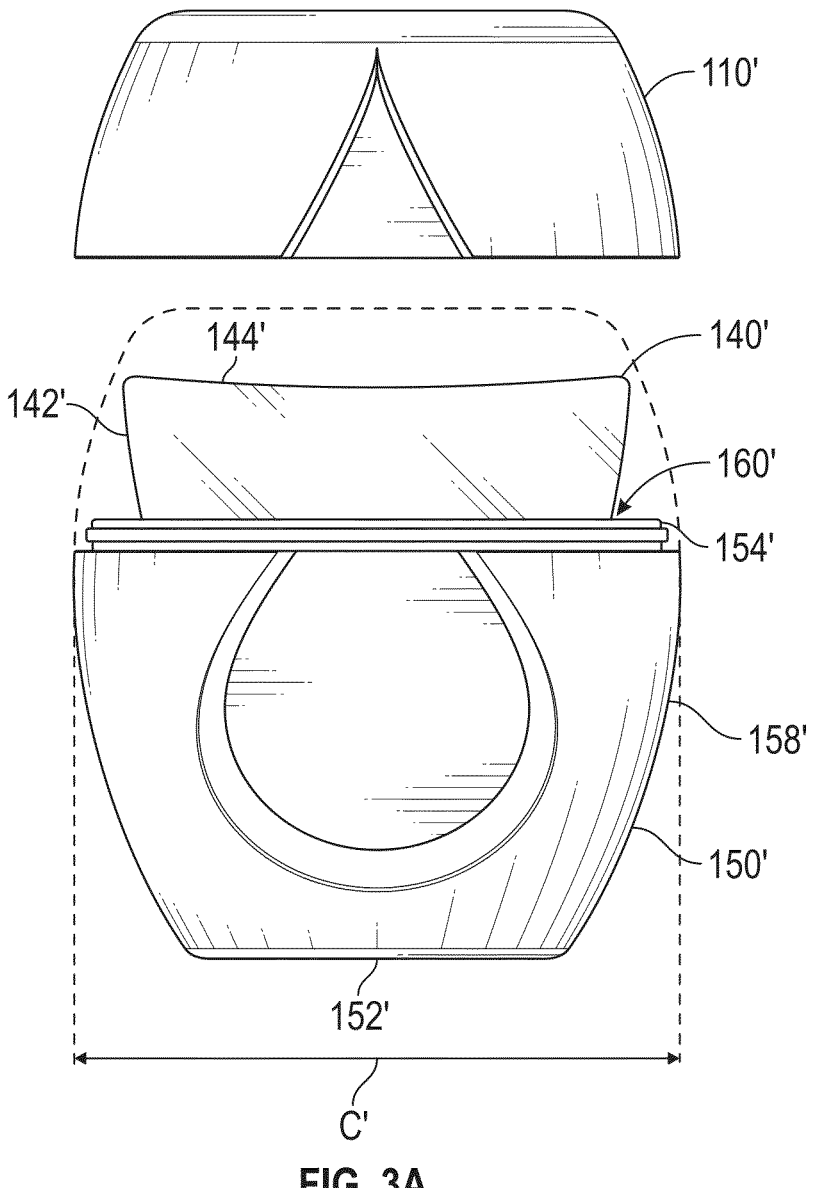
FIG. 3A is a schematic front view of the eye drop dispenser assembly of FIG. 1B with its cap removed and spaced above the dispenser bottle, the dashed line showing the outline of the cap when covering the eye cup.

FIG. 3A depicts a front view of the dispenser assembly 100' shown in FIG. 1B with the cap 110' removed. The assembly 100' has a dispenser bottle 150 comprising a base 152' connected to a side wall 158'. The dispenser bottle 150' has a nipple 130' projecting from a surface 164' (e.g., a recessed surface) of the dispenser bottle 150' that is at an opposite end of the dispenser bottle 150' (e.g., distal) from a base 152'. The nipple 130' can have a circular profile, as shown for example in FIG. 4B; however, the nipple 130' can have other suitable shapes. The dispenser bottle 150' also has a shoulder 154' circumferential to a second surface 160' and distal to the base 152', as shown in FIG. 3A. The side wall 158' also connected to the second surface 160'. In some embodiments, the shoulder 154' is disposed to extend above the second surface 160'. In other embodiments, the shoulder 154' is formed integral to the second surface 160' (e.g., the second surface 160' forms the upper surface of the shoulder 154' such that when the cap 110' is on, the second surface 160' fits within the cap 110' rather than the cap 110' sitting on the second surface 160'). The second surface 160' is parallel to the base 152'. In the illustrated arrangement, shown in FIG. 3C, the assembly 100' also includes an eye cup 140'. The eye cup 140' is fixedly coupled to the dispenser bottle 150'. When the cap 110' is coupled to the dispenser bottle 150', the eye cup 140' can fit within the cap 110'. The eye cup 140' has a circumferential wall 142' and an edge 144' (e.g., a top edge) that is distal to the dispenser bottle 150'. In one example, the eye cup 140' (e.g., the circumferential wall 142') tapers toward the second surface 160'.

With reference to FIG. 3A, the assembly 100' has a width C'. In one implementation, the width C' is between 1.5 and 2.5 inches, such as 1.9 inches.

Figure 3B:
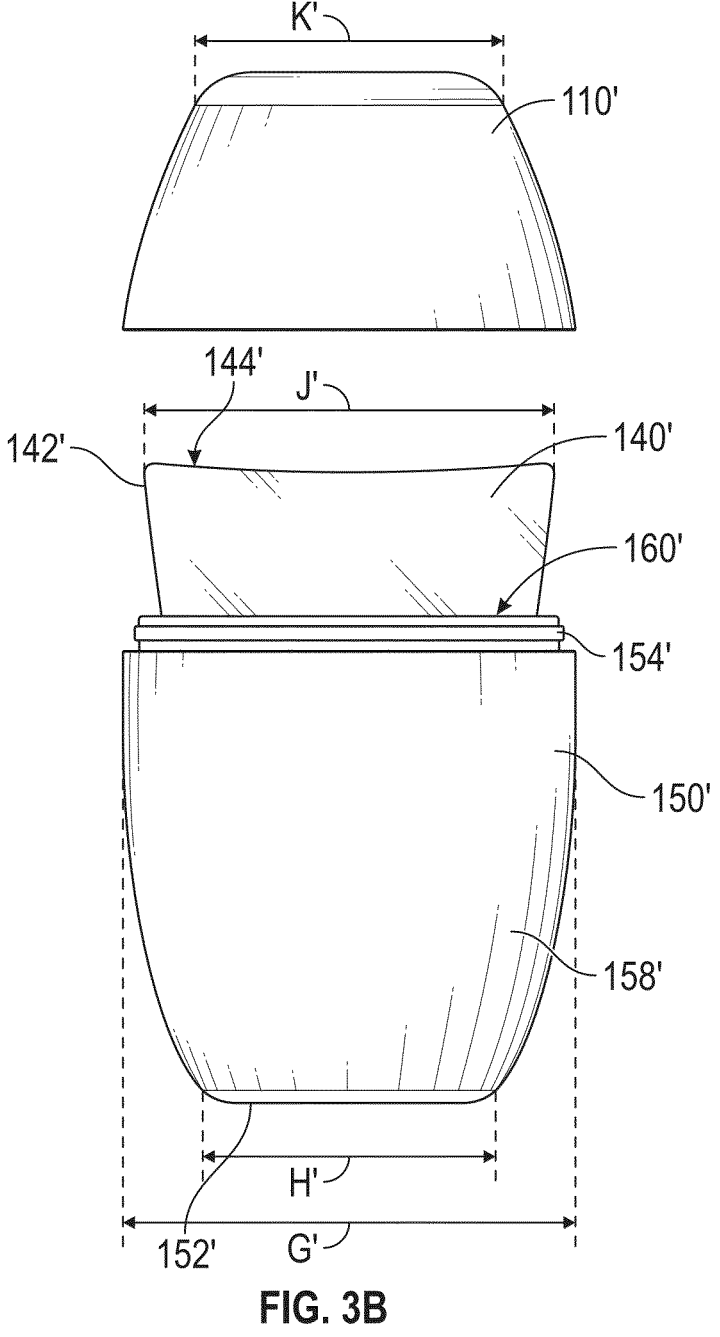
FIG. 3B is a schematic side view of the eye drop dispenser assembly of FIG. 1B with its cap removed and spaced above the dispenser bottle.

With reference to FIG. 3B, the assembly 100' has a depth G'. The base 152' has a depth H'. Depth G' may be larger than depth H'. In one implementation, the depth G' is between 1 and 1.5 inches, such as 1.2 inches and the depth H' is between 0.5 and 1 inches, such as 0.8 inches. The eye cup 140' has a depth J'. Depth J' may be smaller than Depth G'. In one implementation, the depth J' is between 1 and 1.25 inches, such as 1.1 inches. The cap 110' has a depth K' (at its distal end). In one implementation, the depth K' is between 0.5 and 1 inches, such as 0.9 inches.

Figure 3C:
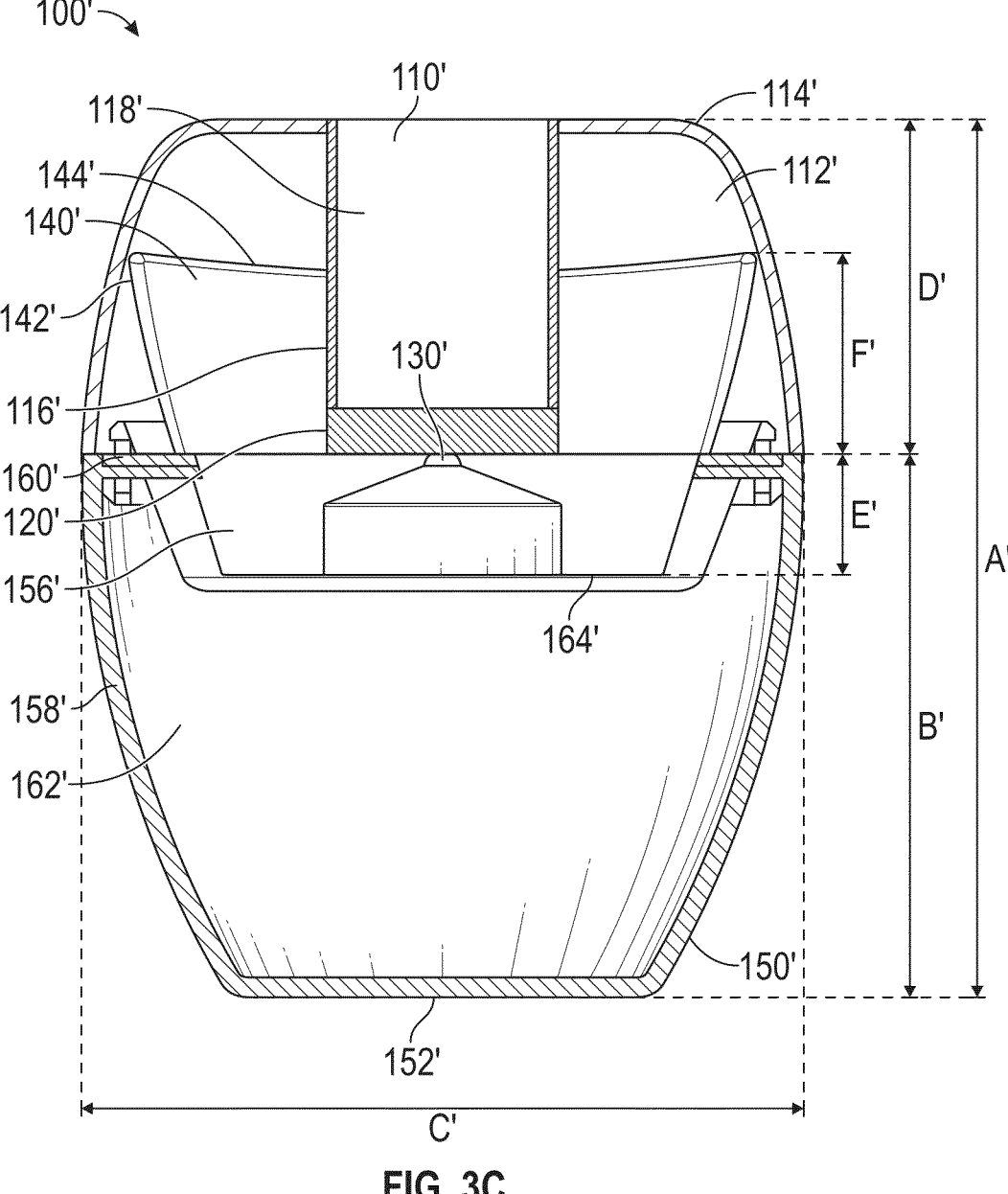
FIG. 3C is a schematic cross-sectional view of the eye drop dispenser assembly of FIG. 1B, where the section line is through the midplane of the side view in FIG. 3B.

FIG. 3C depicts a cross-sectional view of the dispenser assembly 100' shown in FIG. 3A. The section is taken at a midpoint of the depth G' of the assembly 100' (see FIG. 3B). The dispenser bottle 150' has a chamber 162' that can hold a liquid. The cap 110' is connected to the dispenser bottle 150'. The dispenser bottle 150' has a nipple 130' projecting from a surface 164'. The surface 164' is between the second surface 160' and the base 152'. The positioning of the surface 164' creates a recess 156' around the nipple 130'. The recess 156' extends into the dispenser bottle 150' and away from the distal edge 144' of the eye cup 140'. The positioning of the recess 156' allows the nipple 130' to be recessed proximal (e.g., the nipple 130' is nested in the recess 156' of the dispenser bottle 150') to the dispenser bottle 150' while projecting towards the distal edge 144' of the eye cup 140', allowing the dispenser assembly 100' to be more compact than the dispenser assembly 100. The eye cup 140' fits within a cavity 112' of the cap 110' and the circumferential wall 142' defines an oval shape surrounding the nipple 130'. The nipple 130' is disposed between distal edge 144' of the circumferential wall 142' and the surface 164' of the dispenser bottle 150'. In one example, the circumferential wall

142' is partially disposed within the recess 156'. The cap 110' has an outer cap 114' that defines the cavity 112'. Within the cavity 112', is a post 118' extending from the outer cap 114'. In one example, the post 118' is solid. In another example, the post 118' includes a hollow portion (e.g., at a distal end of the post 118'). The post 118' has a seal 120' at its distal end. In one example, the seal 120' is separate from the post 118' and is disposed within the hollow portion (e.g., distal hollow portion) of the post 118'. In another example, the seal 120' is separate from the post 118' and is attached to an end of the post 118'. In another example, the seal 120' is integral (e.g., one piece, monolithic) with the post 118' (e.g., the seal 120' is a distal portion of the post 118' and made of the same material as the post 118'). The outer cap 114' is disposed around the shoulder 154' of the bottle 150'. The post 118' and the seal 120' define an inner cap 116'. The seal 120' sits adjacent the top of the nipple 130' and presses against the nipple 130' to inhibit leakage of a solution or liquid from the nipple 130'. In one example, the seal 120' can have a shape similar to (e.g., a mirror image of) a shape of the nipple 130'). The post 118' is disposed within the eye cup 140' when the cap 110' is connected to the dispenser bottle 150'.

In the illustrated arrangement, the bottle 150' has a height B' measured from the base 152' to the second surface 160'. In one implementation, the height B' is between 1 and 1.5 inches, such as 1.25 inches. The assembly 100' has a height F' (for the eye cup 140') measured from the surface 164' to the distal edge 144'. In one example, the eye cup 140' extends from the second surface 160' (e.g., the eye cup 140' is outside the recess 156'). In another example, the eye cup 140' extends from the surface 164' so that at least a portion of the circumferential wall 142' of the eye cup 140' is in the recess 156' of the bottle 150'. In one implementation, the height F' is between 0.25 and 0.75 inches, such as 0.4 inches. The assembly 100' also has a height D'. Height D' is the height of the cap 110'. The height D' is greater than height F'. In one implementation, the height D' is between 0.5 and 1 inches, such as 0.75 inches. The dispenser bottle 150' has a height E' measured from the second surface 160' to the surface 164'. In one implementation, the height E' is between 0.1 and 0.4 inches, such as 0.25 inches. In some arrangements, the second surface 160' may be coplanar with the surface 164' and height E' is zero inches. In some examples, the second surface 160' and the surface 164' can be portions of the same surface.

Figures 4A, 4B:
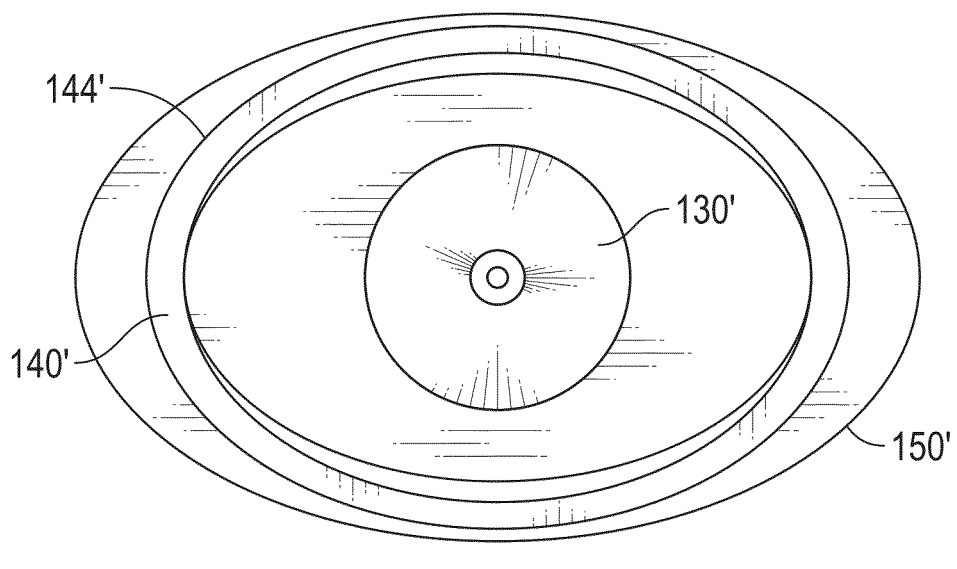
FIG. 4A is a schematic top view of the eye drop dispenser assembly of FIG. 1A.
FIG. 4B is a schematic top view of the eye drop dispenser assembly of FIG. 1B.

FIG. 4A depicts a top view of the assembly 100. The dispenser bottle 150 is shown with the distal edge 144 of the eye cup 140 comprising an oval shape and disposed around the nipple 130. In this embodiment, the dispenser bottle 150, has an oval shaped perimeter. In other implementations, the perimeter of the dispenser bottle 150 or eye cup 140 may take different forms (e.g. substantially polygonal, or substantially circular).

FIG. 4B depicts a top view of the assembly 100'. The dispenser bottle 150' is shown with the distal edge 144' of the eye cup 140' comprising an oval shape and disposed around the nipple 130'. In this embodiment, the dispenser bottle 150', has an oval shaped perimeter. In other implementations, the perimeter of the dispenser bottle 150' or eye cup 140' may take different forms (e.g. substantially polygonal, or substantially circular).

Figure 5A:
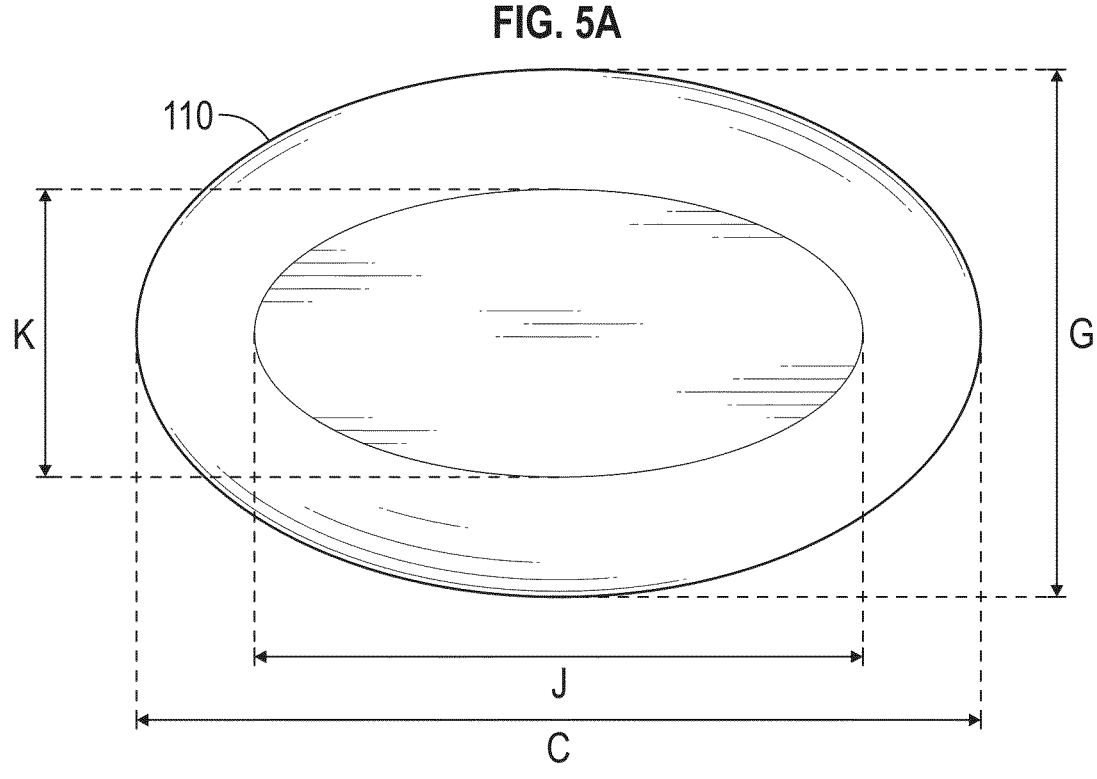
FIG. 5A is a schematic top view of the cap of the eye drop dispenser assembly of FIG. 1A and FIG. 1B.
Figure 5B:
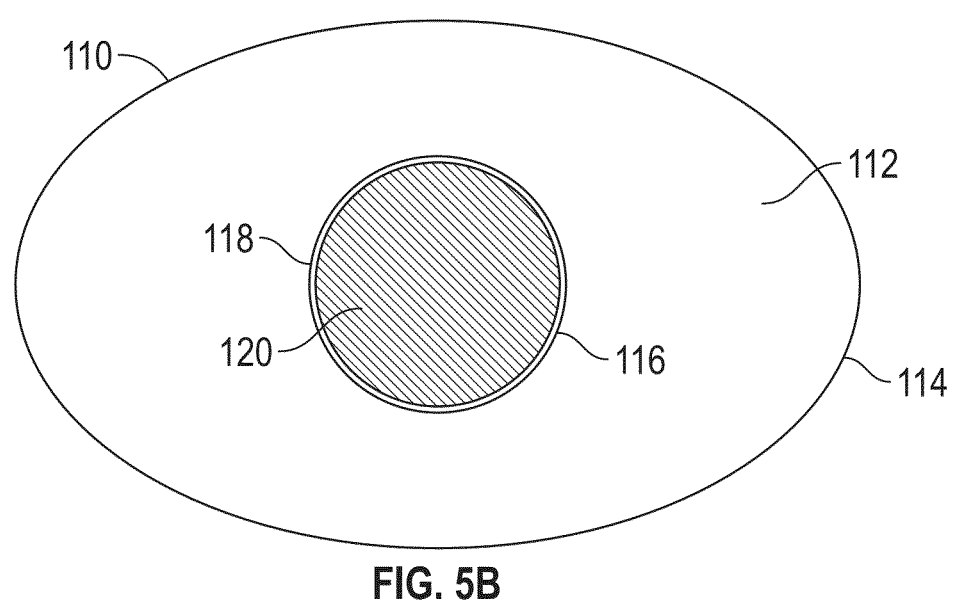
FIG. 5B is a schematic bottom view of the cap of FIG. 5A.
Figure 5C:
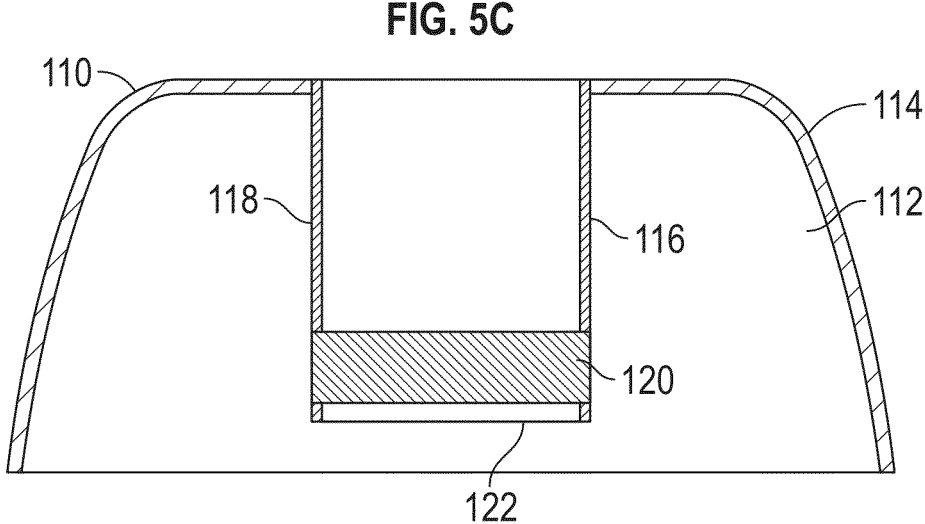
FIG. 5C is a schematic cross-sectional view of the front view of one embodiment of the cap of FIG. 5A, where the section line is through the midplane of the side view.
Figure 5D:
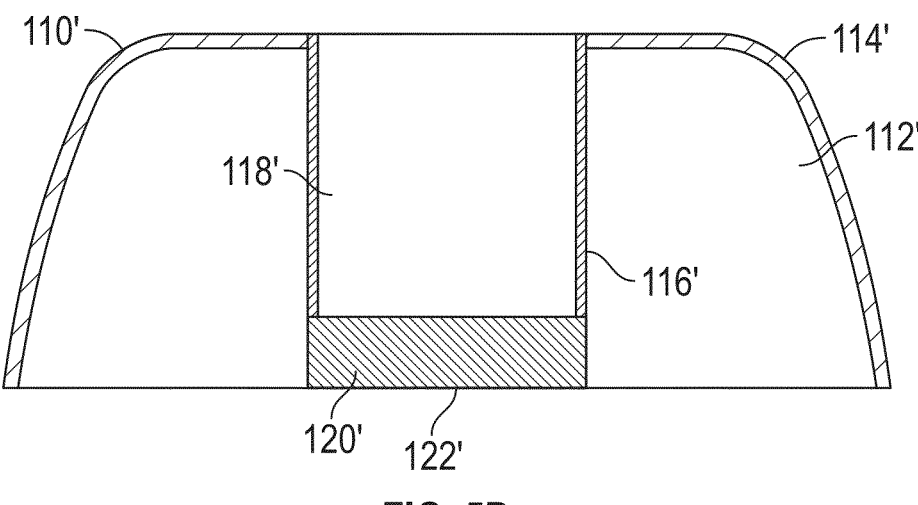
FIG. 5D is a schematic cross-sectional view of the front view of a second embodiment of the cap of FIG. 5A, where the section line is through the midplane of the side view.

FIGS. 5A-5D depict the cap 110. FIG. 5A depicts a top view of the cap 110 and FIG. 5B depicts a bottom view of the cap 110. It is understood that this illustration can be either of the embodiments shown in FIGS. 1A and 1B. FIG. 5C depicts a cross-sectional front view of one embodiment of the cap 110 and FIG. 5D depicts a cross-sectional front view of another embodiment of the cap 110. It is understood that FIGS. 5A and 5B may depict either the embodiment in 5C or the embodiment in 5D.

In the arrangement illustrated in FIG. 5A, the cap 110 has an oval shaped perimeter. In other implementations, the perimeter of the cap 110 may take different forms (e.g., substantially polygonal, or substantially circular). The perimeter of the cap 110 has width C and a depth G. In one implementation, the width C is between 1.5 and 2.5 inches, such as 2 inches and the depth G is between 1 and 1.5 inches, such as 1.25 inches. The top of the cap 110 has a substantially flat surface with an oval shaped perimeter. The perimeter has a width J and a depth K. In one implementation, the width J is between 1.2 and 1.6 inches, such as 1.4 inches and the depth K is between 0.5 and 1 inches, such as 0.7 inches.

FIG. 5B depicts the bottom view of the arrangement illustrated in FIG. 5A. The cap 110 has an outer cap 114, an inner cap 116 extending within the outer cap 114, and a seal 120 recessed in the inner cap 116. The outer cap 114 defining a cavity 112 and the inner cap 116 defined by a post 118.

FIG. 5C depicts a cross-sectional front view of one embodiment of the cap 110. In this embodiment, the post 118 extends into the cavity 112 and the seal 120 sits within the post 118. In one example, a distal portion 122 of the post 118 extends past the seal 120.

FIG. 5D depicts a cross-sectional front view of a second embodiment of the cap 110'. In this embodiment, the post 118' extends into the cavity 112' and the seal 120' sits within the post 118'. The seal 120' extends to the extent of the post 118' (e.g., the seal 120' is at the distal end 122' of the post 118') and the post 118' extends to the extent of the cavity 112'.

In some embodiments, the outer cap 114, the inner cap 116, and the seal 120, or any combination thereof, may be formed as a single piece. The single piece can be an integrated assembly of several parts or can be a unitary structure formed from a single piece of material. In some embodiments, the seal 120, the outer cap 114, and the inner cap 116 may be made from metal, plastic, rubber, or any suitable material. Any of these portions may be made from the same material or from different materials.

Figure 6:
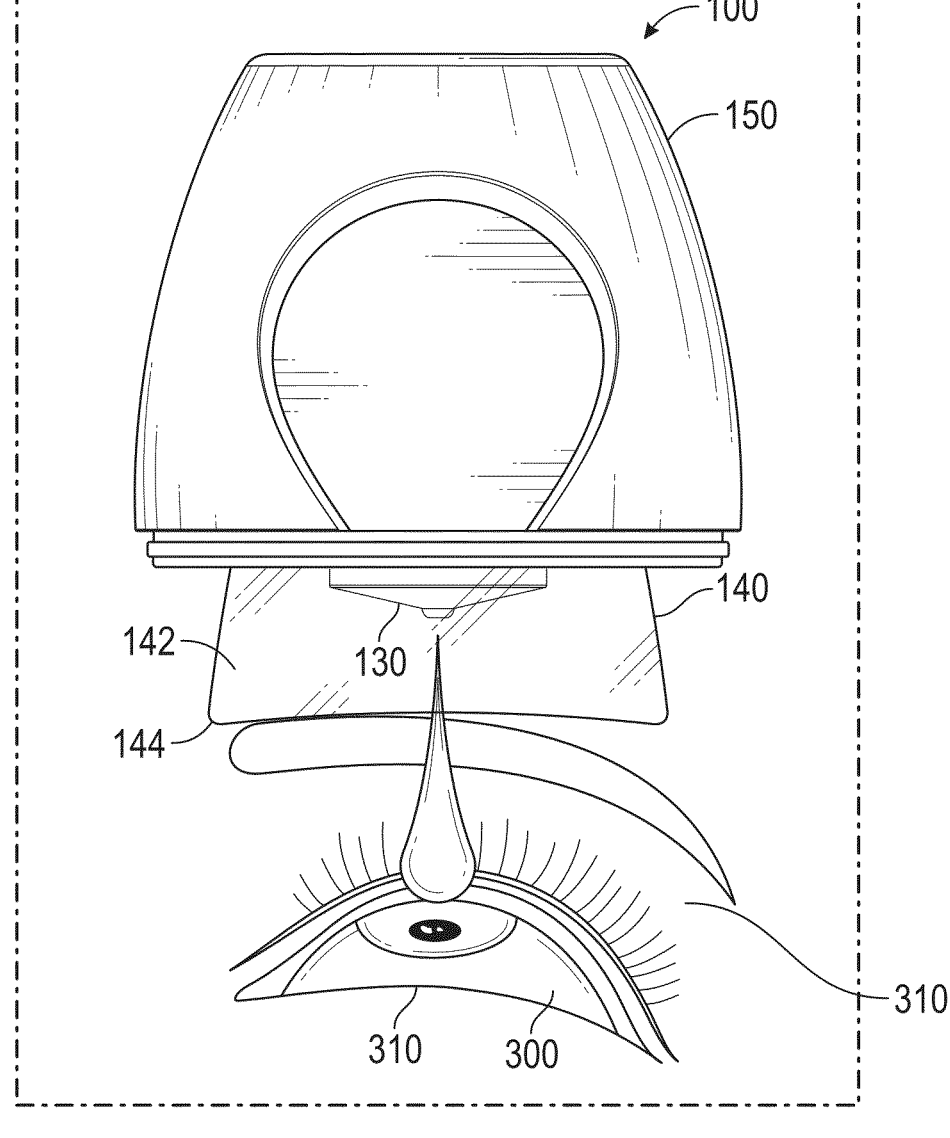
FIG. 6 is a schematic view of the eye drop dispenser of FIG. 1A in an inverted position over a user's eye to deliver an eye drop thereto.

As shown in FIG. 6, the assembly 100 can be inverted and disposed over an eye 200 so that the eye cup 140 is disposed over (e.g., in contact with) an eye socket 210 of the eye 200 (e.g., to that the eye cup 140 provides a supporting structure that supports the dispenser bottle 150 in an inverted position on the eye socket of the user's eye). The user can then squeeze the dispenser bottle 150 to dispense one or more drops into the eye 200. This arrangement advantageously facilitates self-administration of a solution to a user's eye 200 and is user friendly as it does not require the user to assemble the eye cup onto the bottle. Rather, the user simply removes the cap 110 from the dispenser bottle 150, inverts the dispenser bottle 150, places the eye cup 140 against the eye socket of the eye, and squeezes the dispenser bottle 150 to dispense the solution. Further, the nipple 130 is advantageously centered relative to the eye cup 140 so that when the eye cup 140 is supported on the eye socket 210, the nipple 130 is generally aligned (e.g., centered) relative to the eye 200, further ensuring the dispensed solution will be delivered onto or over the eye 200. Advantageously, the eye cup 140 is sized to dispose the distal edge 144 over (e.g., in contact with) the periorbital region 210 and align the nipple 130 with the center of the eye 200. The distal edge 144 of the eye cup 140 is contoured to fit around the periorbital region 210, advantageously allowing the eye cup 140 to comfortably sit or rest over the eye socket 210. This positioning facilitates alignment of the nipple 130 with the eye 200 allowing for dispensing the eye drop(s) directly into the eye 200. This positioning limits (e.g., prevents) waste from having the eye drops fall on the user's face, cheek, eyebrow, ear, etc. Though FIG. 6 depicts the use of the assembly 100, the assembly 100' can be used in the same manner and the advantages listed above also apply to the assembly 100'.

The contour of the distal edge 144 is defined by two axes. The first axis is defined by the nipple 130 such that the distal edge 144 is contoured circumferentially around the nipple 130. The second axis is defined by a point in space approximating the centroid of the external curvature of a user's periorbital region 210. The distal edge 144 is contoured relative to this axis such that the eye cup 140 fits against the user's face. The ability of the eye cup 140 to sit or rest over the periorbital region 210 advantageously facilitates use of the eye drop dispenser assembly 100 by a user with hand tremors, nervous disorders or children to dispense eye drops into the eye. Additionally, supporting (e.g., sitting or resting) the eye cup 140 over the eye socket 210 can inhibit (e.g., prevent) injury to the eye during delivery of eye drops and inhibit the nipple 130 from touching the user's eye 200, thereby inhibiting (e.g., preventing) contamination of the eye 200.

The assembly 100' differs from the assembly 100 in that the dispenser assembly 100' has a smaller external envelope. This is accomplished by recessing the nipple 130' as depicted in FIG. 3C. This allows height D' to be less than height D and height A' to be less than height A. Bottle 150 can hold a larger volume of fluid than bottle 150'.

The assembly 100, 100' is advantageously easy to use (e.g., it is easy to remove the cap 110, 110', position the eye cup 140, 140' over the eye 200, and dispense drops in the optimal location without contaminating the nipple 130, 130'). For example, because the eye cup 140, 140' is integrated (e.g., fixed) with the dispenser bottle 150, 150', the user can simply remove the cap 110, 110', invert the dispenser bottle 150, 150' and position it over (e.g., in contact with) their eye socket 210 and squeeze the dispenser bottle 150, 150' to dispense the solution from the dispenser bottle 150, 150'. Additionally, the fixed eye cup 140, 140' advantageously reduces the likelihood that the eye cup 140, 140' will be lost, use improperly, or that the nipple 130, 130' will be contaminated.

While certain embodiments of the inventions have been described, these embodiments have been presented by way of example only and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

Of course, the foregoing description is that of certain features, aspects and advantages of the present invention, to which various changes and modifications can be made without departing from the spirit and scope of the present invention. Moreover, the devices described herein need not feature all of the objects, advantages, features and aspects discussed above. Thus, for example, those of skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed devices.

What is claimed is:

1. A dispenser assembly, comprising:

a dispenser body and a nipple through which a solution is dispensed, the nipple projecting from the dispenser body; and an eye cup fixedly coupled to the dispenser body, and disposed around the nipple the eye cup comprising:

a circumferential wall; and a distal edge configured to be disposed over an eye socket to facilitate delivery of the solution into a user's eye, wherein the nipple is disposed between the distal edge of the circumferential wall and the dispenser body, wherein the dispenser body has a recess extending away from the distal edge of the eye cup, the nipple projecting towards the distal edge of the eye cup from a surface of the recess, and wherein the circumferential wall of the eye cup is partially disposed within the recess.

2. The dispenser assembly of claim 1, wherein the dispenser body further comprises a flat base.

3. The dispenser assembly of claim 2, wherein the surface of the recess is parallel to the flat base.

4. The dispenser assembly of claim 1, further comprising a cap removably disposed over the nipple.

5. The dispenser assembly of claim 4, wherein the cap comprises a seal disposed adjacent to the nipple to inhibit leakage of solution from the nipple when the cap is disposed over the nipple.

6. The dispenser assembly of claim 1, wherein the nipple is centered relative to the eye cup.

7. The dispenser assembly of claim 1, wherein the dispenser body is flexible.

8. The dispenser assembly of claim 1, wherein the circumferential wall of the eye cup extends out of the recess.

9. The dispenser assembly of claim 1, wherein the circumferential wall of the eye cup tapers outward toward the distal edge.

10. The dispenser assembly of claim 1, wherein the eye cup is configured to inhibit the nipple from touching the user's eye.

11. The dispenser assembly of claim 1, wherein the distal edge is contoured circumferentially toward the nipple.

\* \* \* \* \*